United States Patent [19]

Kretz

[11] 4,135,406
[45] Jan. 23, 1979

[54] METHOD FOR ULTRASONIC EXAMINATION

[75] Inventor: Carl Kretz, Zipf, Austria

[73] Assignee: Kretztechnik Gesellschaft m.b.H., Zipf, Austria

[21] Appl. No.: 781,334

[22] Filed: Mar. 25, 1977

[30] Foreign Application Priority Data

Apr. 8, 1976 [AT] Austria ................................ 2564/76

[51] Int. Cl.² .......................................... G01N 29/04
[52] U.S. Cl. .................................................. 73/620
[58] Field of Search .................. 73/67.8 S, 67.9, 618, 73/619, 620, 621; 128/2 V, 2.05 Z

[56] References Cited

U.S. PATENT DOCUMENTS

| | | | |
|---|---|---|---|
| 3,693,414 | 9/1972 | Soldner | 73/67.9 |
| 3,805,596 | 4/1974 | Klahr | 73/67.8 S |
| 3,895,525 | 7/1975 | Eichelberger et al. | 73/67.9 |
| 4,010,634 | 3/1977 | Baumgartner | 73/67.8 S |

*Primary Examiner*—James J. Gill
*Attorney, Agent, or Firm*—Kurt Kelman

[57] ABSTRACT

A three-dimensional region of an object is scanned with at least one pulsed ultrasonic beam. Echo signals are generated, which represent echoes that have originated within said region in response to said beam. By a switching operation in accordance with at least one logical function, those of said echo signals are selected which represent echoes that have originated at at least one locus that is defined by said at least one logical function. Each of the thus selected echo signals is displayed at a location which is coordinated with the location at which the echo represented by said signal has originated.

9 Claims, 11 Drawing Figures

METHOD FOR ULTRASONIC EXAMINATION

This invention relates to a method of examining objects by means of projected and reflected ultrasonic pulses, in which sound beams are projected into the object from one or more sound transducer heads, which are adjustable by a sound transducer head-positioning mechanism, and echo signals are displayed on fluorescent screens at locations which are coordinated with the locations at which the echoes have originated in the object.

For numerous examinations of objects, e.g., for medical examinations, pictures of the interior of an object are required. All known processes have the disadvantage that a three-dimensional body cannot be represented by a two-dimensional picture without loss of information. In ultrasonic examinations it has been attempted to improve the accuracy of the results by displaying a plurality of pictures taken in different directions, when this is possible. This practice cannot always be adopted, and it has been necessary to display the pictures in succession. This always involves difficulties in clearly coordinating the positions of the several pictures. Besides, soft regions of the body which are subjected to medical examination may be changed by such examination (during an examination of the abdomen even the pressure applied by the sound transducer head may slightly deform soft parts). For these reasons the previous methods of examination often do not permit of a definite coordination of individual portions of pictures taken in succession. Besides, the production of each picture takes a certain time so that the overall time required is much increased when a plurality of sectional plane pictures must be made. As the equipment, which is rather expensive, is occupied for a long time for the examination of a single patient, the method which has been described can hardly be adopted for serial examinations.

Whereas such X-ray picture represents a certain volume, all successive layers in the direction of irradiation are projected onto a plane so that the information related to the depth of each layer is lost. This information can be retrieved if a plurality of pictures are taken from different directions, but this will greatly increase the radiation dose absorbed by the patient.

In the previous use of the ultrasonic method of producing section plane pictures, the section plane which is displayed is inherently determined by the direction of the beam projected from the sound transducer head and by the displacement of the sound transducer head and the sound beam transversely to the direction in which it is projected. When the observation of a B display picture produced by this method of examination suggests that an examination of a slightly different section plane would result in an improved representation, the examination must be repeated and an attempt must be made to find the more favorable section plane. To enable a comparison of section plane pictures produced in succession, the usual practice has been to take photographs of each picture which has been produced by an individual examination so that the overall time required and the costs of the examination are further increased.

In a method of the kind described first hereinbefore, the invention resides essentially in scanning a certain three-dimensional region of the object with one sound beam or a plurality of sound beams and utilizing logical switching circuitry connected to the output of the ultrasonic equipment to define one or more sectional planes and/or lines of intersection in the object, which definition is independent of the surface of the object, the direction of the sound beam, and the direction in which the sound transducer head is displaced by the sound transducer head positioning mechanism, and to select the signals associated with the sectional planes and/or lines thus defined from among all signals which have been received, and to apply only the thus selected signals to the fluorescent screen or screens in groups associated with respective sectional planes and/or lines of intersection, so that section plane or A display pictures are represented.

In the method according to the invention, two or more sectional planes pictures of different section surfaces can be displayed at the same time. Besides, it is possible to derive other displays, such as A display pictures, from interesting regions. It is even possible to produce pictures of sectional planes which are oblique to the directions in which the sound beam is emitted and propagated. At the beginning of an examination, the position of the sectional planes which would furnish most information is not known in most cases. In accordance with the invention, a certain three-dimensional region is examined and the sectional planes can be selected and changed without need for a re-adjustment of the sound transducer head-positioning mechanism. By means of an A display picture, the amplitudes of the echoes from predetermined regions can be represented in addition to the sectional plane pictures.

The selected sectional planes and/or lines of intersection defined by means of the logical switching circuitry in the three-dimensional region in which the object is to be examined are preferably adjusted independently of each other and of the displacement of the sound transducer head. In practice the logical switching circuitry will be used to select at least two sectional planes which intersect in the three-dimensional region to be examined so that the object is examined, e.g., in longitudinal and transverse sectional planes.

A still more accurate representation will be obtained if the line of intersection of two intersecting sectional planes is displayed in the section plane pictures which are displayed. This display will facilitate also the selection of a sectional plane. In a preferred practice, two sectional planes which intersect at right angles to each other are defined by the logical switching circuitry and the corresponding sectional plane pictures are displayed. A display picture relating to the line of intersection of said section planes can also be displayed. This mode of display is similar to the well-known representation in accordance with the rules of descriptive geometry and facilitates the analysis of the sectional plane pictures.

Whereas a separate fluorescent screen may be provided for each picture, such arrangement will be complex and highly expensive and will require a coordination of the means for adjusting the picture tubes. For this reason it is preferred to display the pictures simultaneously on a single fluorescent screen of a cathode ray tube, to associate a certain area of the fluorescent screen with each picture, and to apply those signals which have been selected by the logical switching circuitry to the input of the cathode ray tube by means of controlled switches which succeed said logical switching circuitry. In known manner, the echo-originating locations in the examined three-dimensional region may be defined by location-defining voltages and the coordinates of the selected sectional planes and/or lines of intersection may be defined by adjustable locus-defining voltages.

According to a further feature of the method according to the invention, the echo signals produced in the examination are stored in a storage device at addresses which are coordinated with the locations at which the echoes have originated and an address-selecting computer constituted by the logical switching circuitry is used to read from said storage device those signals which are stored at addresses associated with selected lines of intersection and/or sectional planes. In such arrangement, the ultrasonic equipment and the sound transducer head-positioning mechanism may be used to take within a relative short time a record of all interesting data which are associated with a virtually instantaneous condition of the three-dimensional region to be examined. When this record has been taken in a medical examination, the patient may be dismissed. The interesting data which have been recorded are subsequently analyzed. For this analysis, any desired sectional planes and section lines can be selected.

Further details of the invention will become apparent from the following description of the accompanying drawings, in which the invention is illustrated by way of example.

Figure 1:
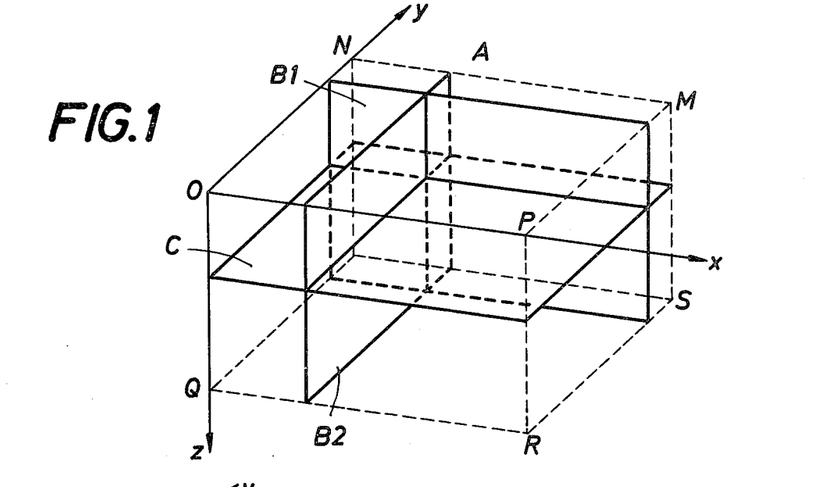
FIG. 1 is a diagrammatic perspective view for an explanation of the geometrical relationships.

In FIG. 1, the three-dimensional region to be subjected to a single examination is diagrammatically indicated by a cube having corners MNOPQRST. The sound transducer head is applied to the face MNOP and is moved to project a beam downwardly, in the direction of the z-axis. Three sectional planes in said three-dimensional region are selected and displayed. These sectional planes are designated B1, B2 and C in FIG. 1, and it is assumed that they can be shifted within the three-dimensional region which is shown so that the position of the planes depends on the adjustment selected for a given examination and need not always be the same as shown on the drawing. The A display picture should represent that portion of the three-dimensional region under examination which corresponds to the line of intersection A of planes B1 and B2. This association has been selected for practical reasons. For an examination, the three section planes will be selected so that all of them intersect the tissue portion to be examined so that said tissue portion lies in the system of coordinates defined by the three lines of intersection as coordinate axes. Owing to the coordination which has been selected, the A display reliably represents this tissue portion too. Because the line of intersection between the examined planes is to be displayed too, the location to which the A display is related is also immediately displayed in this way. In accordance with the terminology currently used in connection with ultrasonic examination, section plane pictures related to planes in which the sound beam is propagated are described as B display pictures and pictures related to planes which extend at right angles to the sound beam as C display pictures. When the section planes are displayed in the mode that has been selected, two B display pictures B1 and B2 are obtained as well as a C display picture C.

Figures 2, 3:
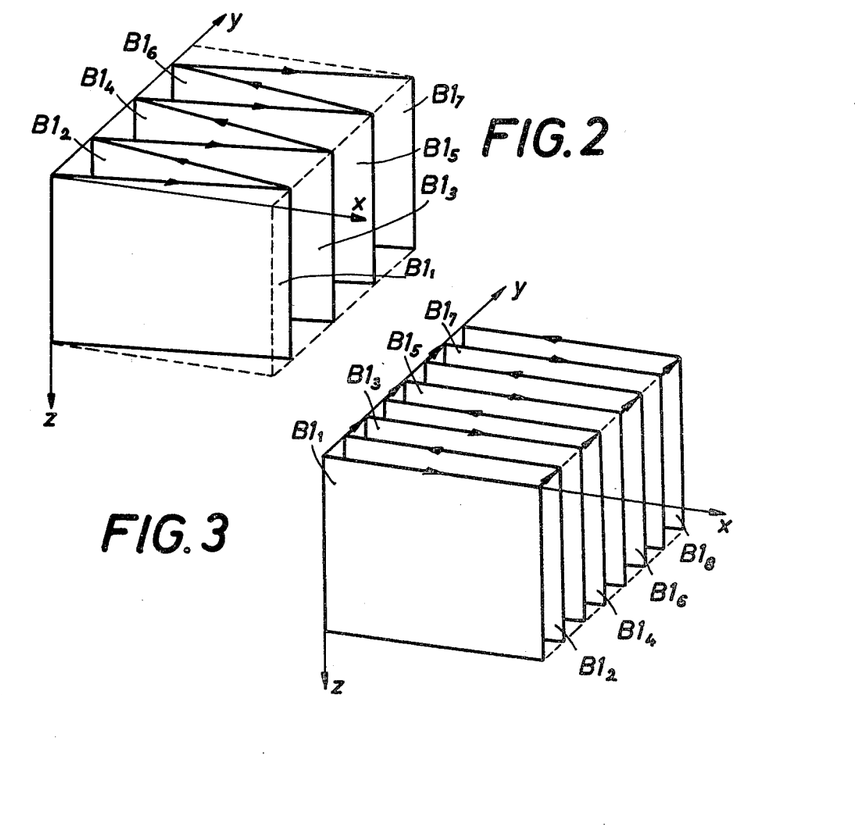
FIGS. 2 to 7 are diagrammatic views which represent certain modes of scanning three-dimensional regions to be examined.

In carrying out the method, the three-dimensional region to be examined need not be defined by parallel sectional planes, as is shown in FIG. 1, but three-dimensional regions having other shapes may be selected. This will be explained more fully in the following examples. FIGS. 2 and 3 are based on the assumption that a sound transducer head is moved in the x-y plane in such a manner that the head is always displaced parallel to itself. The movement is composed of a fast oscillatory movement in the x-direction and of a slower movement in the y-direction. The resulting path of the sound transducer head in the x-y plane corresponds approximately to the zig-zag line shown in FIG. 2. When the sound transducer head projects sound in the direction of the z-axis, a number of alternately pairs of parallel sectional planes $B1_1$ to $B1_7$ are defined within the three-dimensional region under examination. As will be explained hereinafter, these sectional planes will be much closer together in practice than is shown on the drawing for the sake of clearness. If the movement in the y-direction is not continuous but intermittent and takes place whenever the movement in the x-direction is being reversed, the sound transducer head will move along the meandering path shown in FIG. 3 and the several sectional planes $B1_1$ to $B1_8$ will be parallel to each other and to the x-z plane.

Figure 4:
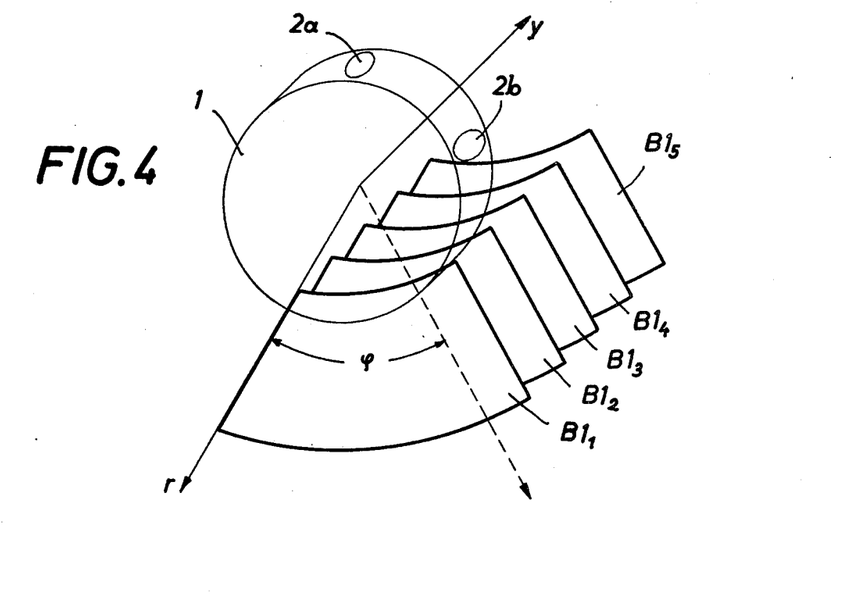
Figure 5:
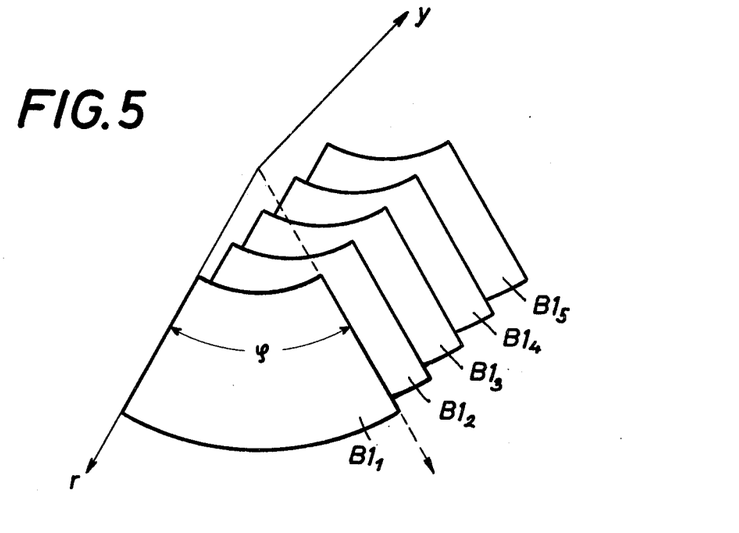

FIGS. 4 and 5 illustrate a scanning of a three-dimensional region under examination with a plurality of sound transducer heads disposed at the periphery of a rotating wheel 1. The axis of the wheel 1 extends in the y-direction. During its rotation about its axis, the wheel is displaced in the y-direction. Two of the sound transducer heads mounted at the periphery of the wheel are indicated and designated 2a and 2b, respectively. Suitable circuitry ensures that only one sound transducer head is activated during a predetermined portion of a revolution. This operation results in a definition of a series of sector-shaped sectional planes surfaces $B1_1$ to $B1_5$. As is shown in FIG. 4, these sectional planes will not be at right angles to the y-axis when the wheel is continuously displaced in the y-direction. When the displacement consists of successive steps performed during the switching interval between the activation periods of successive sound transducer heads, the scanning pattern shown in FIG. 5 will be obtained, in which sector-shaped section planes which are at right angles to the y-axis will be obtained.

Figure 6:
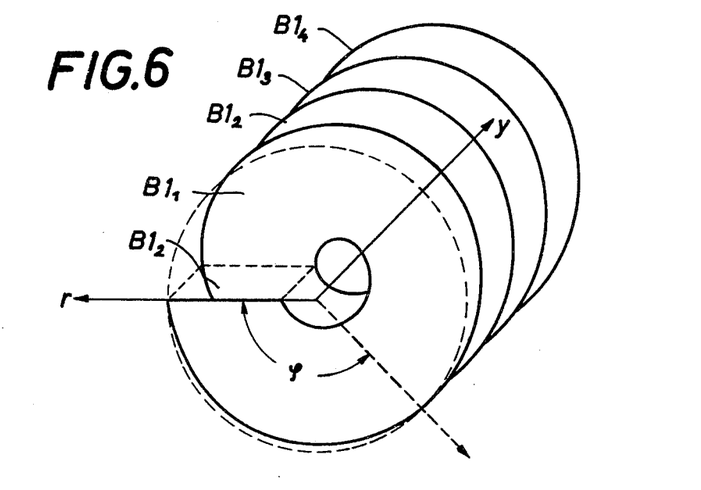
Figure 7:
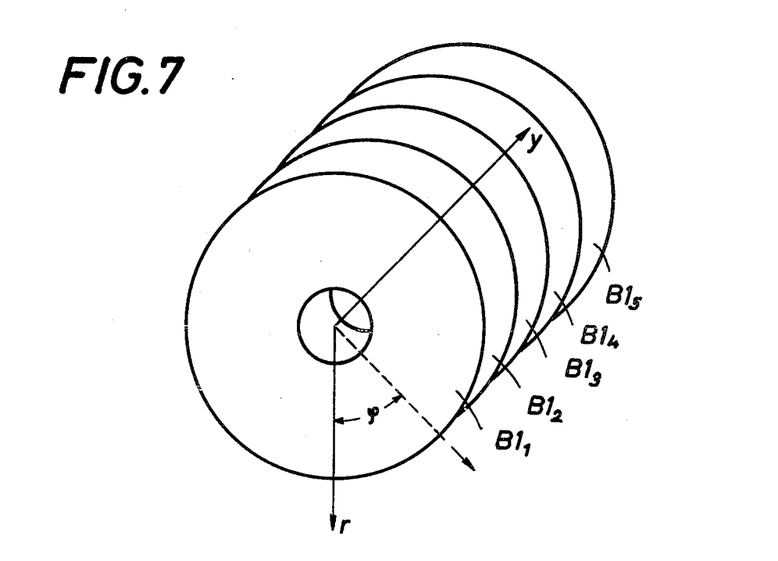

FIGS. 6 and 7 illustrate a scanning pattern which is obtained by means of a rod-shaped probe which projects sound in a radially outward direction. Such probes set with sound transducer heads are introduced into cavities of the body for a scanning with outwardly projected sound. When the rod is rotated and longituidinally displaced at the same time, the scanning pattern shown in FIG. 6 results. In this case, the body is no longer scanned in discrete planes but in a helicoid which may be imagined to be composed of planes $B1_1$ to $B1_4$. The fact that strictly speaking the individual planes are not planes but elements of a helicoid is hardly significant in practice because the pitch is much smaller than is shown on the drawing. On the other hand, planes can also be scanned in this case when the advance in the y-direction is performed in steps after each complete revolution. This will result in the parallel circular sectional planes which are shown in FIG. 7.

When the sound transducer head performs a movement which involves an angular movement of the sound beam rather than a displacement parallel to itself, cylindrical coordinates y, r, and q will be preferred to cartesian coordinates for the further considerations. Because this is not significant for the principle of the method, the relationships will be explained hereinafter in most cases with reference to cartesian coordinates.

Whereas the three-dimensional region examined in accordance with FIGS. 2 and 3 is prismatic, FIGS. 4 and 5 illustrate the examination of a sector of a cylinder and FIGS. 6 and 7 the examination of a complete cylinder. In all methods, the three-dimensional region is scanned in a series of successive sectional planes, which are more or less parallel. The required spacing of these planes will be discussed with reference to FIG. 3 and these teachings are applicable to all other modes of scanning.

When it is assumed that the depth of the region to be examined, i.e., its dimension in the z-direction, is 300 mm, the time required by the sound for its return trip from the lowest plane, at the velocity of sound in the tissue amounting to 1500 m/s, is calculated as 400 microseconds. In the case assumed, this will be the largest permissible time interval between successive sound pulses if the occurrence of so-called echoes is to be avoided. The corresponding pulse repetition frequency is 2.5 kHz. To provide for a margin of safety, a somewhat lower frequency, e.g., of 2 kHz, will probably be selected. It may also be assumed that the movement in the x-direction should be 100 mm and 20 section planes should be scanned per second. As a result, one sound pulse is projected, on an average, after a displacement of the sound transducer head in the x-direction by 1 mm so that each section plane is scanned along lines which are spaced 1 mm apart. Whereas that line pattern may appear coarse at first sight, it must be borne in mind that sound beams which are a few millimeters in diameter are usually employed so that a finer line pattern would not result in an improvement. If the B2 plane is to be scanned in the same density as the B1 plane, the several B1 planes must also be spaced 1 mm apart. This spacing is much smaller than is shown in FIGS. 2 to 7. Whereas the B1 and B2 planes are scanned in a line pattern, the C plane is scanned in a dot pattern, which is defined by the points at which the C plane is penetrated by the lines from the several B1 planes. In this case the dot density in the x-direction corresponds to the line density in the B1 plane and the dot density in the y-direction depends on the spacing of the successive B1 planes. The B1 and B2 planes need not be scanned with the same line density. This line density may be increased or decreased by a selection of the spacing of the several B1 planes.

To produce the various section plane pictures and the A display picture, the data which result from the scanning of the three-dimensional region must be selected and displayed in such a manner that corresponding pictures result. Each point which is scanned within the three-dimensional region is defined by four parameters, which consist of the space coordinates $\dot{x}$, $\dot{y}$, and $\dot{z}$ of the location and the amplitude A of the echo from said location; this amplitude may be zero, of course. Coordinates $\dot{x}$ and $\dot{y}$ are determined by the position of the sound transducer head, and coordinate $\dot{z}$ is determined by the travel time of the sound. It is known in the art to transform said parameters into corresponding parameters x, y, z and A, which can be represented on the fluorescent screen of a cathode ray tube. This is performed in all section plane display equipment and also A display equipment which is presently manufactured. For this reason the further explanation may be based on the assumption that four signals x, y, z and A are associated with each location which is scanned within the three-dimensional region under examination and these four signals must be processed for the display of the corresponding pictures. To that end, only those locations which lie in one of the three selected planes must be selected from the large number of scanned locations, and the signals associated with the selected locations must be processed to produce the desired display.

Figure 8:
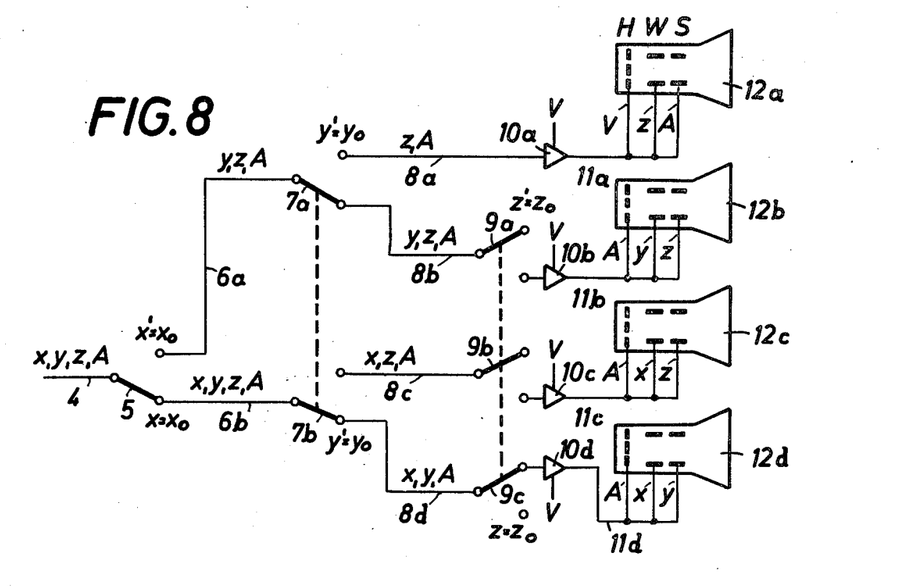
FIG. 8 is a circuit diagram showing logical switching circuitry to be used where pictures are to be displayed on a plurality of fluorescent screens.

The sequentially operated, logical switching circuitry shown in a simplified representation in FIG. 8 is provided for this purpose. The circuitry basically comprises three series-connected switch groups 5, 7 and 9. Each of the switches shown comprises a plurality of poles equal in number to the signals to be switched. The switches of each switch group 5; 7a, 7b; 9a, 9b, 9c can assume two states, which are respectively represented by upper and lower positions. The switch will assume the state represented by the upper position when a prescribed equation condition is fulfilled, and the other state in all other cases. How this control is performed will be explained hereinafter and is assumed to be known at this juncture. The switches of the first switch group are in the state represented by the upper position when $\dot{x} = x_o$ and in the state represented by the lower position when $\dot{x} - x_o$. Hence, when the sound transducer head is in an arbitrarily selected position $x_o$, the signals x, y, z and A arriving via respective leads, which are represented by a single line 4, will be transmitted to line 6a, possibly with the exception of signal x, which is not required for the display. In the position shown, the input signals are transmitted to line 6b because the condition $x = x_o$ is not fulfilled. Lines 6a and 6b are further branched by switches 7a and 7b, which will assume the state represented by the upper position when $\dot{y} = y_o$ and the state represented by the lower position when $\dot{y} - y_o$. This results in a further distribution of the signals to the lines 8a to 8d. The signals are further distributed by the switch group 9a to 9c in dependence on the conditions $\dot{z} = z_o$ and $\dot{z} - z_o$.

The signals which have been transmitted by the logical switching circuitry are applied to adding amplifiers 10a to 10d, in which a predetermined bias voltage V is added to each signal. The output signals of these adding amplifiers are transmitted in lines 11a to 11d to respective electrodes of the cathode ray tubes.

FIG. 8 shows a brightness control grid H, horizontal deflection electrodes W and vertical deflection electrodes S. The bias voltages are added to the signal voltages for two reasons: The bias voltages control the position of the picture on the fluorescent screen so that said position can be suitably adjusted. Besides, in case of the absence of a signal voltage, e.g., because a switch group is just interrupting the lines concerned, the bias voltage prevents the electrodes from assuming an undefined potential which would result in uncontrolled displays.

In the position shown, the conditions $\dot{x} - x_o$, $\dot{y} - y_o$, and $\dot{z} = z_o$ are fulfilled so that only those signals are initially applied only to cathode ray tube 12c which come from a depth $z = z_o$. This is independent to a high degree from the position of the sound transducer head so that a C display picture is traced. The lines will be interrupted only when the sound transducer head assumes a position in which its x-coordinate equals $x_o$ and/or its y-coordinate equals $y_o$. In these two cases, the tracing of the C display picture will be interrupted. The resulting lines in the picture represent exactly the lines of intersection between the plane represented by the C display picture and the planes represented by the B1 and B2 display pictures. It is apparent that the logical switching circuitry does not only transmit the signals to the corresponding picture tubes but ensures also that the lines of intersection between the planes represented by the several pictures are displayed at the same time.

It is apparent that $x_o$, $y_o$, and $z_o$ are the coordinates of the planes which are to be displayed and these planes can be shifted by a change of said parameters. When the states assumed by the several switches in all conceivable positions of the sound transducer head are considered, it will be found that there are numerous positions in which no signal line is connected to any cathode ray tube. In that case the signals received by the sound transducer head are associated with locations which lie in the scanned three-dimensional region but do not lie in at least one of the selected section planes.

With the scanning line density which has been assumed in the example, the scanning of the entire three-dimensional region would take 2 to 5 seconds, depending on its extent in the y-direction. This would mean that either the several pictures are traced with such intervals of time or the tracing of the entire picture would take that time so that cathode ray tubes having a corresponding persistence time would have to be used.

In the embodiment shown in FIG. 8, four cathode ray tubes 12a to 12d are used and each picture is displayed on a separate fluorescent screen. On the other hand, the display of the pictures on four separate tubes does not facilitate the analysis and greatly increases the expenditure.

Figure 9:
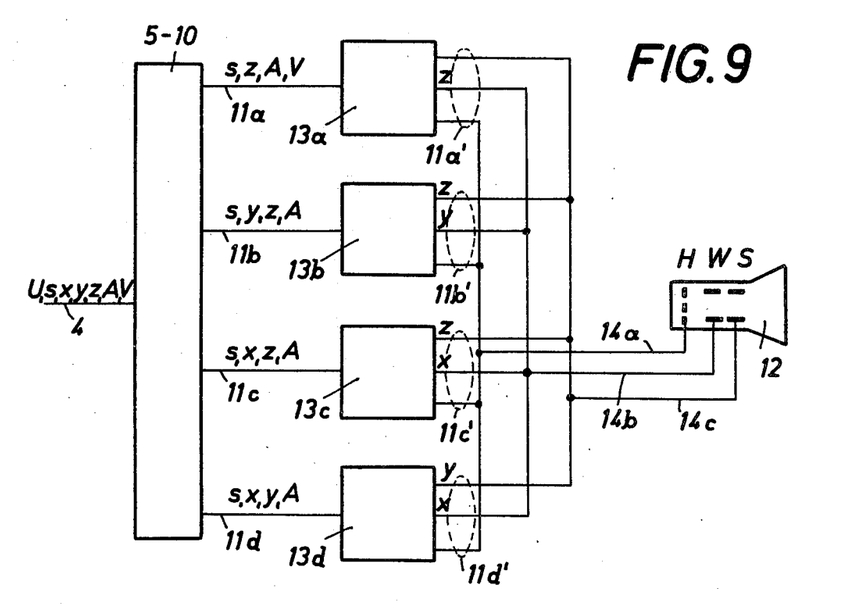
FIG. 9 shows circuitry which permits of a display of a plurality of pictures on a common fluorescent screen.

For this reason, FIG. 9 illustrates a modified circuit arrangement in which all pictures are displayed on the screen of a single cathode ray tube 12. This can be accomplished without loss of information if the fluorescent screen is sufficiently large. In FIG. 9, the logical switching circuitry inclusive of the adding amplifiers is combined in the switch group designated 5 to 10. The only difference from the arrangement of FIG. 8 resides in that an additional gating d.c. voltage s must be switched together with the signals so that an additional pole is required in each switch. A selecting voltage U serves to actuate the logical switching circuitry and is not shown in FIG. 8 because nothing has been said about the control of the switches. In fact, three selecting voltages are required for the respective switch groups 5, 7 and 9, respectively. The bias voltages V are not switched but are directly applied to the adding amplifiers included in the switching circuitry 5 to 10. The output voltages of the switching circuitry are first transmitted in lines 11a to 11d to switches 13a to 13d, which are designed to interrupt the connections to the cathode ray tube when the gating voltage s is switched together with the signal voltages, as has been mentioned, the cathode ray tube is connected at any given time only to the lines in which echo signals are being transmitted. A formation of loops will be avoided because the logical switching circuitry ensures that echo signals are transmitted only in one line at any given time. The several pictures displayed on the fluorescent screen of the cathode ray tube will be juxtaposed and for this reason can be more easily compared.

Figure 10:
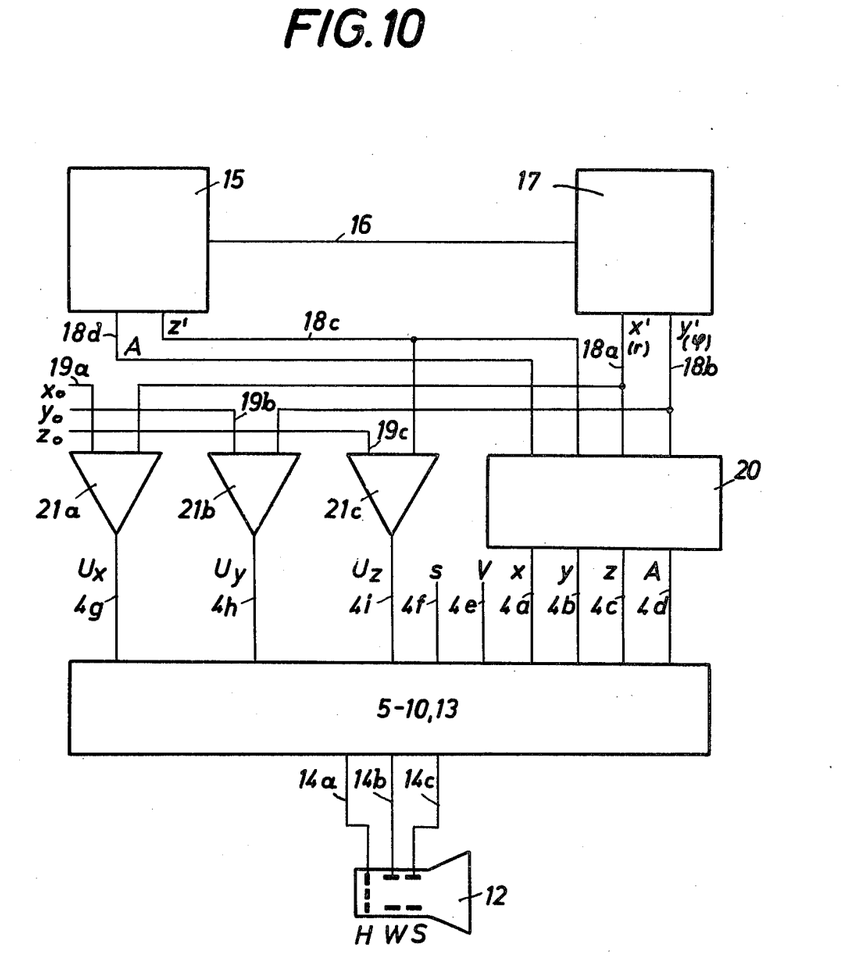
FIG. 10 is a block diagram showing an entire equipment used for examination.

FIG. 10 represents an overall circuit arrangement and illustrates also the control of the logical switching circuitry. A signal emitting and echo signal-processing unit 15 is connected by a line 16 to a sound transducer head which is mounted in a positioning mechanism 17. Via the line 16, the unit 15 transmits control pulses to the sound transducer head and receives pulses representing the echoes which have been received by the sound transducer head. The positioning mechanism moves the sound transducer head and at the time delivers signals which represent the positon $\dot{x}$, $\dot{y}$ of the sound transducer head. In case of an angular movement, the parameters $\dot{x}$ and $\dot{y}$ would be replaced by $\dot{r}$ and $\dot{q}$. A signal $\dot{z}$ which represents the transit time of the emitted and reflected sound is derived from the sweep voltage in the ultrasonic unit, which produces also a voltage A that represents the echo amplitude. All these signals are transmitted in lines 18a to 18d to a location-responsive computer 20, which amplifies the signals into the ranges of magnitude which are required for a sweep of the picture area. The amplified output signals x, y, z, and A of the computer are transmitted in lines 4a to 4d to the logical switching circuitry. The signals $\dot{x}$, $\dot{y}$, and $\dot{z}$ representing the location coordinates are transmitted not only to the location-responsive computer 20 but also to voltage comparators 21a to 21c and are compared therein with arbitrarily adjusted voltages $x_o$, $y_o$, and $z_o$. When any two voltages which are compared are equal in magnitude, the respective comparator produces a selecting voltage $U_x$, $U_y$ or $U_z$, which is transmitted via the respective line 4g, 4h or 4i to the logical switching circuitry and in the latter controls the corresponding switches.

The switch groups 5, 7, and 9 (FIG. 8) are respectively controlled by selecting voltages $U_x$, $U_y$, and $U_z$. The logical switching circuitry is also supplied with the above-mentioned bias voltages V via line 4e and with the gating voltages s via line 4f. The operation then proceeds as described in connection with FIGS. 8 and 9. At this juncture it should be mentioned that electronic switches rather than mechanical switches will be preferred in the logical switching circuitry because they permit of a higher switching frequency. The selected reference voltages $x_o$, $y_o$, and $z_o$ define the section planes to be represented, and these voltages can be changed to shift the section planes without a change of adjusted position of the mechanism for positioning the sound transducer head.

In the use of the arrangement just described, the sound head mechanism must be applied to the object, consisting of a patient in the case of a medical examination, and is operated throughout the examination. The sound transducer head receives a large number of echo signals which are not required for the display of a picture and for that reason are lost. For this reason, an improvement of the process has been developed by the provision of a circuit arrangement with which all received signals can be initially stored and the signal values can subsequently be read from the storage device in that sequence in which they are required for the display of the corresponding pictures. Because the reading is not destructive, the storage device can be searched as often as desired in different directions whereas the patient need no longer be irradiated. Because the reading of the storage device can be performed much faster than the recording in the storage device, the picture frequency of the display unit may be increased to such an extent that long-persistence tubes are not required.

Figure 11:
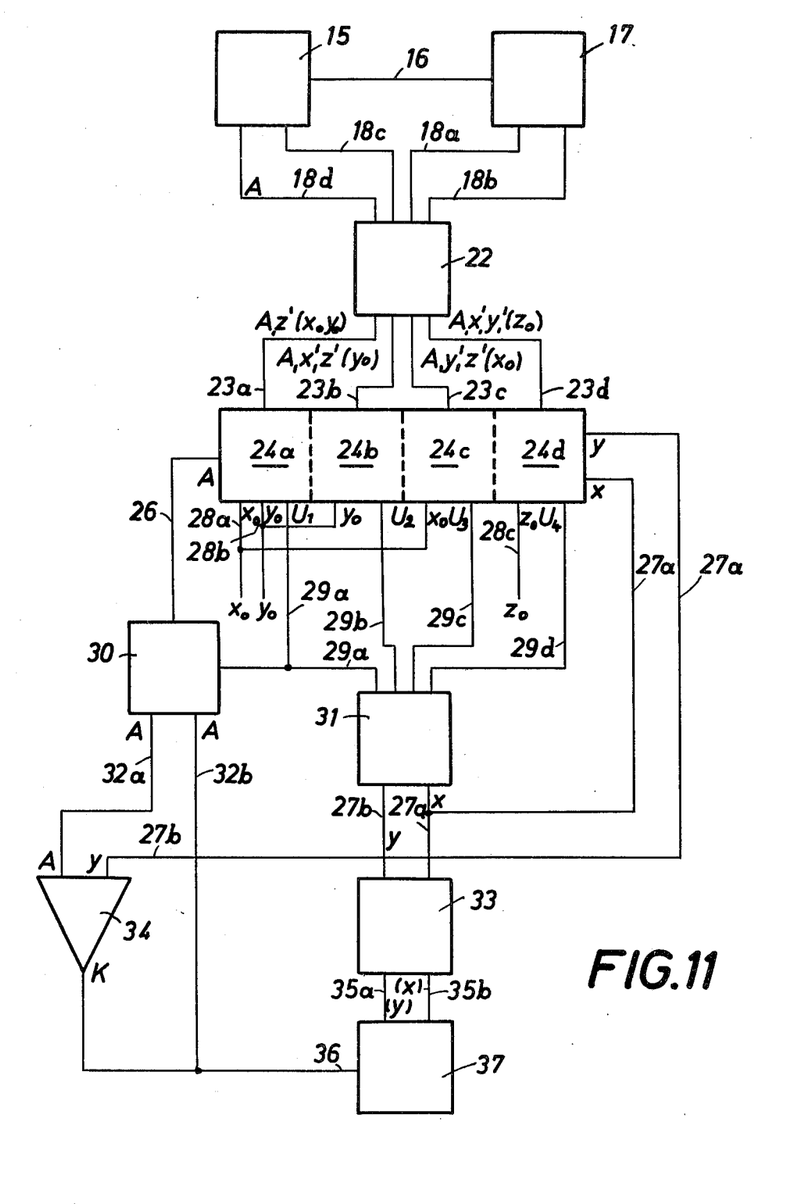
FIG. 11 is a diagram representing equipment used for examination and comprising a storage device.

FIG. 11 shows such circuit arrangement for a display on a television monitor. For this reason, the storage device is to be read with a line sequence which is in accordance with television standards. The ultrasonic processing unit 15 and the mechanism 17 for positioning the sound transducer head deliver the signals $\dot{x}$, $\dot{y}$, $\dot{z}$, and A which are to be analyzed. These signals are initially stored in a storage device 22 in such a manner that each amplitude parameter A is stored at an address defined by the parameters $\dot{x}$, $\dot{y}$, and $\dot{z}$. The reading of the storage device is controlled by a horizontal and vertical sweep generator 33 in accordance with television standards. That generator produces a horizontal sweep voltage X and a vertical sweep voltage y. The synchronizing signals are transmitted via lines 35a and 35 b to a television monitor 37 to synchronize the two units.

The voltages are also applied via lines 27a and 27b to a selecting voltage generator 31, which derives from said voltages four selecting voltages $U_1$ to $U_4$ in accordance with the following rule: When the maximum x-voltage is designated X and the maximum y-voltage is designated Y, the following conditions are to be fulfilled:

$U_1$: $X<X/2$ and $y<Y/2$
$U_2$: $x>X/2$ and $y<Y/2$
$U_3$: $x<X/2$ and $y>Y/2$
$U_4$: $x>X/2$ and $y>Y/2$ As a result, one of the four selecting voltages will be applied, depending on the quadrant of the fluorescent screen to which the electron beam is being directed. These selecting voltages are applied via lines 29a to 29d to an address-selecting computer 24a to 24d, which consists of four sections in this case, and activate the corresponding computer section, in which two of the three address parameters for the several addresses in the storage device are now derived from the voltages x and y which are applied to said computer section via lines 27a and 27b. The third address parameter is supplied to the address-selecting computer as a constant or manually adjustable voltage $x_o$, $y_o$ or $z_o$ via lines 28a to 28c. It will be understood that the address-selecting computer 24a to 24d may consist of a single section; in that case the selecting voltages $U_1$ to $U_4$ are applied only to change the reading programs. The adjustable parameters $x_o$, $y_o$, and $z_o$ define the respective section planes to be displayed by the three section plane pictures. The address-selecting computer derives the addresses within said planes from the variable parameters x and y and reads the A values stored at such addresses.

The address-selecting computer is connected to the storage device by lines 23a to 23d. The A values which have been read are transmitted via line 26 to a selector switch 30. When one of the three section plane images is being read, the selecting voltage $U_1$ is not applied and the parameter A is directly transmitted to the television monitor 37 via line 32b and is used in said monitor for a brightness control. On the other hand, if the A display picture is to be traced, the address-selecting section 24a is enabled by the voltage $U_1$ and the selector switch 30 connects the line 26 to the line 32a at the same time. Because for an A display, information stored at addresses relating to a line rather than to a surface must be read from the storage device, the address-selecting computer is controlled only in dependence on the x-voltage whereas the two other address values are maintained by the manually adjusted voltages $x_o$ and $y_o$. Each voltage which has been read is applied to the comparator 34 and is compared therein with the y-voltage from the horizontal and vertical sweep generator. When the two values are equal, a constant voltage K is applied via line 36 to the television monitor and results in a brightening of the electron beam so that the A display picture is traced dot by dot because the electron beam of the television monitor performs a line scan in accordance with the television standard and cannot trace the A display picture as a continuous line as in normal A display units used for ultrasonic examination. By a change of the manually adjustable values $x_o$, $y_o$, and $z_o$, the addresses to be selected in the storage device can be changed as desired so that pictures of different section planes can be displayed. When the three-dimensional region has been scanned once, all values have been stored in equipment which performs that method and a further irradiation of the patient is not required. Thereafter, the entire storage device can be gradually searched for the data required for the various display modes.

It is apparent that the method which has been described results in a simultaneous display of intersection of sectional planes which are preferably at right angles to each other. This mode of representation is similar to the mode of representation used in descriptive geometry and results in a better representation of a three-dimensional region than the previous methods. Besides, the method is faster and permits of a better comparison because the various sectional planes are displayed simultaneously. Because the planes which are displayed can be shifted within the three-dimensional region which is being scanned, the entire region can be quickly scanned for information without a need for complicated readjustments of the mechanism for positioning the sound transducer head.

What is claimed is:

1. An ultrasonic method of examining an object, comprising
    (a) moving a sound transducer head means over the object,
    (b) directing an ultrasonic beam of pulses from the transducer head means into a three-dimensional region of the object to scan the region with the pulses,
    (c) receiving echo pulses originating from the scanned region in the transducer head means and generating therefrom output signals corresponding to the echo pulses,
    (d) connecting a logic circuit to the transducer head means to receive the output signals,
        (1) the logic circuit selecting at least two sectional planes and the line of intersection of the sectional planes in the scanned region, independently of the surface of the object, the direction of the ultra-sonic beam and the movement of the transducer head means, and transmitting only those output signals corresponding to the echo pulses emanating from the selected sectional planes or from one sectional plane and a selected line or lines of intersection of the selected sectional planes, and
    (e) receiving the separately transmitted signals at points of a picture screen geometrically corresponding to the geometric points whence the echo pulses originate in the scanned region to obtain simultaneously from each one of the selected planes or lines a separate corresponding picture on the screen and to show each line of intersection.

2. The ultrasonic examining method of claim 1, wherein the selected planes or lines in said planes are displaced by the logic circuit independently of each other and of the movement of the transducer head means.

3. The ultrasonic examining method of claim 1, wherein the planes are selected to intersect in the scanned region.

4. The ultrasonic examining method of claim 3, wherein the line of intersection of the intersecting planes defines the geometric points whence the echo pulses originate.

5. The ultrasonic examining method of claim 1, wherein two of said sectional planes extending perpendicularly to each other are selected by the logic circuit.

6. The ultrasonic examining method of claim 1, wherein the picture screen is a fluorescent screen of a cathode ray tube, the screen having individual image areas associated with respective ones of the sectional plane pictures, and further comprising the step of switching the transmitted signals from the logic circuit to an input of the cathode ray tube.

7. The ultrasonic examining method of claim 1, wherein the positions of the echo pulses in the scanned region are determined by characteristic voltages and the coordinates of the selected planes or lines are determined by adjustable voltages.

8. The ultrasonic examining method of claim 1, further comprising the steps of storing the output signals according to the locus whence the corresponding echo pulses originate, and incorporating a computer into the logic circuit programmed to transmit only the signals corresponding to the selected planes or lines.

9. The ultrasonic examining method of claim 8, wherein the picture screen is a television screen and the computer is programmed to transmit the signals in accordance with television line sequence standards.

* * * * *